United States Patent
Laskin et al.

(10) Patent No.: US 9,422,233 B2
(45) Date of Patent: Aug. 23, 2016

(54) VANILLOID FATTY HYDROXAMATES AS THERAPEUTIC ANTI-INFLAMMATORY PHARMACEUTICALS

(75) Inventors: Jeffrey D. Laskin, Piscataway, NJ (US); Ned D. Heindel, Easton, PA (US); Carl Jeffrey Lacey, Schnecksville, PA (US); Abhilash N. Pillai, Tiruvalla (IN); Marion Gordon, Princeton, NJ (US); Diane E. Heck, Rumson, NJ (US)

(73) Assignees: RUTGERS, THE STATE UNIVERSITY OF NEW JERSEY, New Brunswick, NJ (US); LEHIGH UNIVERSITY, Bethlehem, PA (US)

( * ) Notice: Subject to any disclaimer, the term of this patent is extended or adjusted under 35 U.S.C. 154(b) by 793 days.

(21) Appl. No.: 13/422,565

(22) Filed: Mar. 16, 2012

(65) Prior Publication Data
US 2012/0252891 A1    Oct. 4, 2012

Related U.S. Application Data

(60) Provisional application No. 61/453,274, filed on Mar. 16, 2011.

(51) Int. Cl.
*A61K 31/27* (2006.01)
*C07C 271/16* (2006.01)
*C07C 259/06* (2006.01)

(52) U.S. Cl.
CPC ............. *C07C 271/16* (2013.01); *C07C 259/06* (2013.01)

(58) Field of Classification Search
CPC .. A61K 31/27; C07C 271/06; C07C 2101/14; C07C 237/22; C07C 271/20; C07C 271/16; C07C 259/06
USPC .................. 514/489, 613, 622; 564/170, 123; 560/115
See application file for complete search history.

(56) References Cited

FOREIGN PATENT DOCUMENTS

GB    WO2010055316 A2 *    5/2010

OTHER PUBLICATIONS

Lee et al (Bioorg. Med. Chem. Lett., 2001, 11, 965-968).*
RN629-04-9, available Nov. 16, 1984, corresponding to 1-bromoheptane.*
RN306-08-1, available Nov. 16, 1984, corresponding to 2-(4-hydroxy-3-methoxyphenyl)acetic acid.*

* cited by examiner

*Primary Examiner* — Jason Sims
*Assistant Examiner* — Ibrahim D Bori
(74) *Attorney, Agent, or Firm* — Fox Rothschild LLP

(57) ABSTRACT

Three unique subtypes of N-hydroxyamides and N-hydroxycarbamates containing both the vanilloid moiety (4-hydroxy-3-methoxybenzyl) and a lipophilic aliphatic moiety. Also disclosed are direct syntheses of these vanilloid fatty hydroxamates. The compounds possess inhibitory activity against the enzymes fatty acid amide hydrolase (FAAH) and matrix metallo-proteinase 9 (MMP-9). In addition, these substances bind to the calcium channel protein TRPV1 and inhibit vesicant-induced inflammation in skin and cornea. The compounds have utility in treating topical or systemic inflammatory processes in the skin and/or eye.

12 Claims, 5 Drawing Sheets

Formula (V)

Type 1:
X = N-OH
Y = -(CO)O-

Type 2:
X = N-OH
Y = CO

Type 3:
X = CO
Y = N-OH

VANILLOID FATTY HYDROXAMATES AS THERAPEUTIC ANTI-INFLAMMATORY PHARMACEUTICALS

CROSS-REFERENCE TO RELATED APPLICATIONS

This application claims benefit of priority under 35 U.S.C. §119(e) of U.S. Provisional Application Ser. No. 61/453,274, filed on Mar. 16, 2011, the entire disclosure of which is incorporated herein by reference.

STATEMENT REGARDING FEDERALLY SPONSORED RESEARCH OR DEVELOPMENT

This invention was made with government support under Contract No. U54AR055073 awarded by the National Institutes of Health CounterACT Program through the National Institutes of Arthritis and Musculoskeletal and Skin Diseases. The government has certain rights in the invention.

FIELD OF THE INVENTION

This invention relates to N-hydroxylated vanilloid fatty amides and N-hydroxylated vanilloid fatty carbamates and their use as anti-inflammatory pharmaceuticals. Methods for preparing these substances are also described.

BACKGROUND OF THE INVENTION

Inflammation is a clinically significant medical dysfunction in numerous topical and systemic diseases and its suppression provides a major therapeutic benefit in the treatment of those conditions. Such conditions include, but are not limited to, chemical insults, autoimmune disease, vasculitis, rheumatoid arthritis, atherosclerosis, asthma, hay fever, acne vulgaris, reperfusion injury, dermal abrasions, psoriasis, burns, blisters, inflammatory bowel disease, Alzheimer's dementia, Parkinson's, and other neurodegenerative disorders.

A pharmacologically-attractive binding target, which has been linked closely to modulation of pain and inflammatory responses, is the transient receptor potential vanilloid (TRPV1) also known as the VR1 or the vanilloid/capsaicin receptor. The latter names derive from the fact that TRPV1 binds both the heat sensation-producing component of pepper (capsaicin) as well as a family of fatty amides carrying the 4-hydroxy-3-methoxybenzylamine (vanilloid) moiety. TRPV1 is a non-selective cation channel gated by extracellular protons, heat, and small molecule amides, thioamides, and ureas containing the 4-hydroxy-3-methoxy-benzyl fragment or a prodrug form of the same entity. This 4-hydroxy-3-methoxybenzyl component, as found in the endogenous ligand capsaicin, when attached to a lipophilic moiety virtually guarantees an association with the TRPV1 channel. In human skin, the dermis and the epidermis are rich with TRPV1 positive cells and in patients who have experienced painful inflammation, there is often a marked up-regulation of this receptor.

Medicinal chemists have manipulated the classic vanilloid fatty amide, capsaicin-like platform (Formula (I), wherein Ar=4-hydroxy-3-methoxyphenyl and R=a lipophilic alkyl or cycloalkyl hydrocarbon construct) in search of medically useful drug candidates, by reversing the orientation of the amide functionality. The thus-derived candidate class (Formula (II), wherein Ar=4-hydroxy-3-methoxyphenyl and R=a lipophilic alkyl or cycloalkyl hydrocarbon construct) has been termed the "retro" isomer.

Ar—CH$_2$—NH—CO—R      Formula (I)

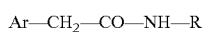

Ar—CH$_2$—CO—NH—R      Formula (II)

Yet another manipulation has been to strategically insert an oxygen atom, thereby converting the traditional fatty acid vanilloid amides into carbamates. In this fashion, analogs of according to Formula (III) and Formula (IV) emerge, both of which possess anti-inflammatory activity.

Ar—CH$_2$—NH—CO—O—R      Formula (III)

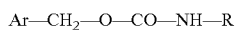

Ar—CH$_2$—O—CO—NH—R      Formula (IV)

Besides TRPV1 as a pharmacological target of merit in pain and inflammation, a case has been made for targeting the matrix metalloproteinases (MMPs), especially MMP-9. MMP-9 has been especially cited as up-regulated in various clinical inflammatory states, and compounds which inhibit MMP-9 display therapeutic potential. The well-known MMP-9 inhibitor, doxycycline, has been shown to be effective in suppressing MMP-9 activated by mustards in vesicant-exposed corneas.

While a variety of molecular architectures have been reported for successful MMP-9 inhibitors, virtually all are chelating agents capable of binding ionic zinc and iron, and among the chelator options the most common construct of all has been the hydroxamic acid (hydroxamate) functionality, viz., —CO—N(OH). The present invention discloses new inhibitors of MMP-9, where the molecular design criteria comprise the inclusion of a hydroxamic functionality proximal to both a lipophilic zone and a substituted phenyl ring.

BRIEF SUMMARY OF THE INVENTION

The general scaffold for the compounds described in this invention, Formula (V) (shown below and in FIG. 1), is highly flexible and embraces, as a minimum, the N-hydroxybenzyl fatty carbamates of Type 1, the N-hydroxybenzyl fatty amides of Type 2, and the N-hydroxy aryl acetic acid amides with a pendant alkyl moiety (Type 3).

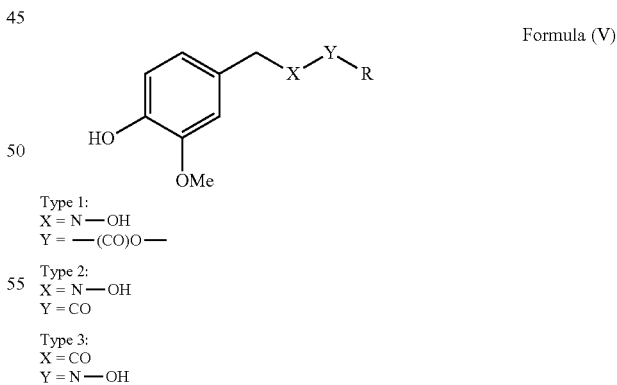

Formula (V)

Type 1:
X = N—OH
Y = —(CO)O—

Type 2:
X = N—OH
Y = CO

Type 3:
X = CO
Y = N—OH

One embodiment of the present invention is directed to a vanilloid fatty N-hydroxy amide or a vanilloid fatty N-hydroxy carbamate compound represented by Formula V, where R is a lipophilic moiety selected from the group consisting of linear and branched alkyl, optionally branched cycloalkyl, linear and branched alkenyl, optionally branched cycloalkenyl, linear and branched alkynyl, optionally substituted aryl, optionally substituted heteroaryl, optionally substituted heteroarylalkyl, and optionally substituted arylalkyl and where either:
(1) X is NOH and Y is (C=O)O (Type 1), or
(2) X is NOH and Y is C=O (Type 2), or
(3) X is C=O and Y is NOH (Type 3).

Type 1 compounds are selected from the group consisting of alkyl-N-hydroxy-N-4-hydroxy-3-methoxybenzylcarbamates. Type 2 compounds are selected from the group consisting of N-hydroxy-N-4-hydroxy-3-methoxybenzylcarboxamides. Type 3 compounds are selected from the group consisting of N-hydroxy-N-alkyl-(4-hydroxy-3-methoxyphenyl)acetamides. A further embodiment of the invention includes prodrugs or pharmaceutically acceptable salts of the compounds of Formula (V).

Another aspect of the invention is directed to a method for preparing a compound of Type 1, comprising the step of reacting a benzylic hydroxylamine with a chloroformate in the presence of magnesium oxide to direct acylation onto the nitrogen atom of the hydroxylamine and thereby yield an alkyl-N-hydroxy-N-benzylcarbamate of formula

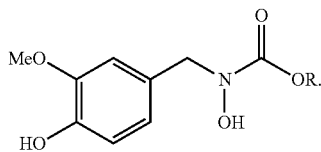

A further aspect of the invention is directed to a method for preparing a compound of Type 2, comprising the step of reacting a benzylic hydroxylamine with an acylated 2-mercapto-thiazoline to direct acylation onto the nitrogen atom of the hydroxylamine and thereby yield an N-hydroxy-N-benzylcarboxamide of formula

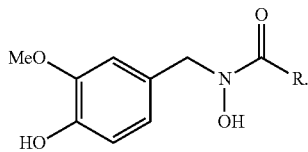

Another aspect of the invention is directed to a method for preparing a compound of Type 3, comprising the steps of:
(a) condensing an aliphatic aldehyde with O-benzylhydroxylamine to form an oxime,
(b) reducing the oxime to an O-benzylhydroxylamine,
(c) condensing the O-benzylhydroxyamine with homovanillic acid (4-hydroxy-3-methoxyphenylacetic acid) to form an amide, and
(d) subjecting the amide to hydrogenolysis to cleave the O-benzyl group and thereby yield the N-hydroxy-N-alkyl(4-hydroxy-3-methoxyphenyl)acetamide of formula

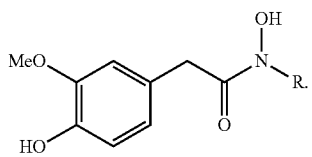

Additional aspects of the invention are drawn to methods of treatment, including:

A method for treatment of a disease state which is influenced by the regulation of FAAH, comprising administering to a patient in need thereof an amount of one or more of the above compounds effective to inhibit fatty acid amide hydrolase (FAAH);

A method for treatment of a disease state in which the regulation of MMP-9 is desired, comprising administering to a patient in need thereof an amount of one or more of the above compounds effective to inhibit matrix metalloproteinase-9 (MMP-9);

A method for treatment of a disease state in which the regulation of an inflammatory response is desired, comprising administering to a patient in need thereof an amount of one or more of the above compounds effective to suppress one or more inflammatory responses;

A method for treatment of a disease state in which inhibition of the separation of the ocular or cutaneous epithelium and stromal layers of the eye is desired, comprising administering to a patient in need thereof an amount of one or more of the above compounds effective to inhibit the separation of the ocular or cutaneous epithelium and stromal layers of the eye; wherein the compound can be formulated as an ophthalmic solution and can be applied topically via dropwise application to the eye;

A method for treatment of a topical or systemic disease state in which inhibition of an inflammatory dysfunction is desired, comprising administering to a patient in need thereof an amount of one or more of the above compounds effective to modulate an inflammatory dysfunction, wherein the compound can be formulated in a dosage form effective to deliver the compound to a desired site;

A method for treatment of injury to skin and/or eyes produced by vesicating agents, corrosive chemicals, or damage-producing substances, comprising administering to a patient in need thereof, an amount of one or more of the above compounds effective to function as an antagonist of the injury caused by vesicating agents, corrosive chemicals, or damage-producing substances, wherein the compound is optionally formulated for effective delivery to the injured site; and A method for treatment of ocular injury produced by vesicating agents, corrosive chemicals, or damage-producing substances, comprising administering to a patient in need thereof, an amount of one or more of the above compounds effective to relieve the ocular injury, wherein the compound can be formulated as an ophthalmic solution and can be applied topically via dropwise application to the eye.

DETAILED DESCRIPTION OF PREFERRED EMBODIMENTS

Figure 1:
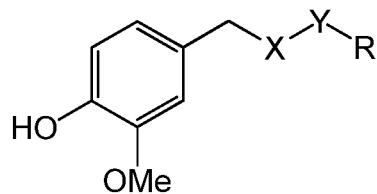
FIG. 1 displays the general chemical scaffold of the compounds of the invention, Formula (V). Three distinct types of molecules are encompassed in Types 1 to 3.
Figure 2:
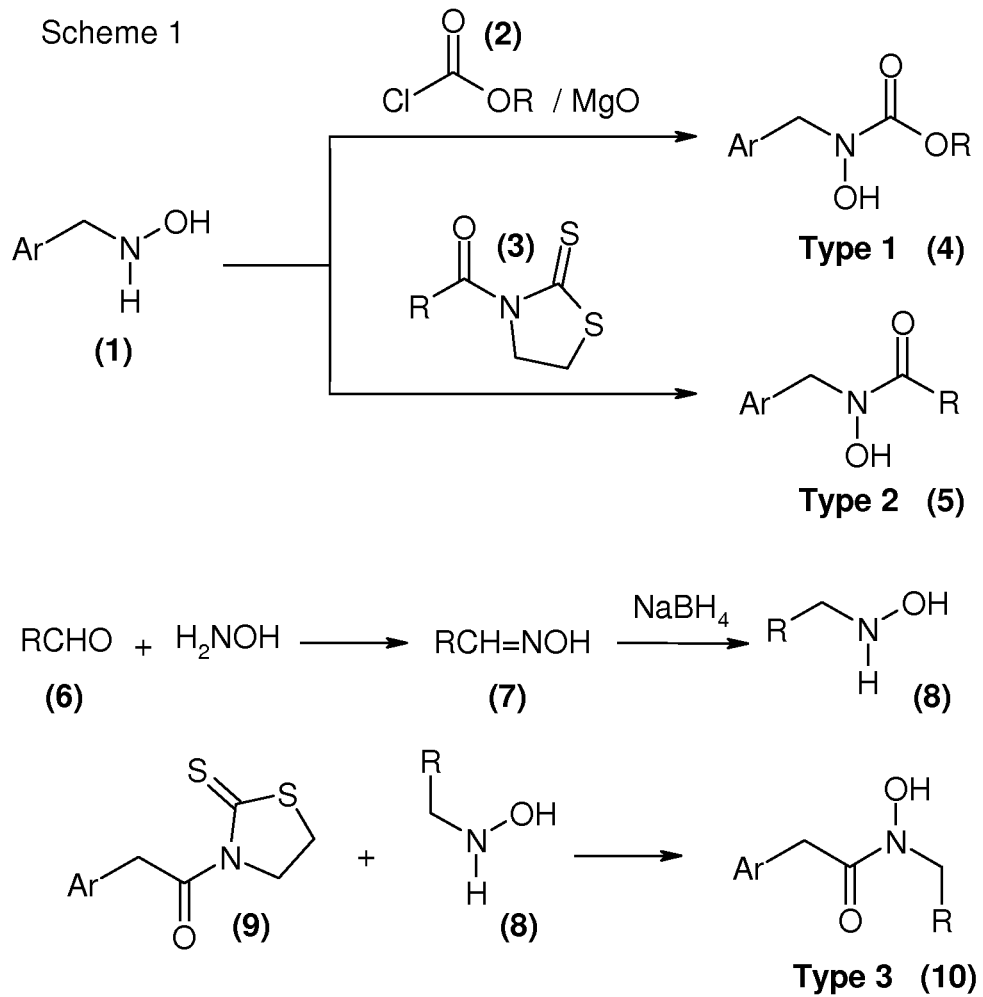
FIG. 2 shows in Scheme 1, the general synthetic route to compounds of Types 1 to 3.
Figure 3:
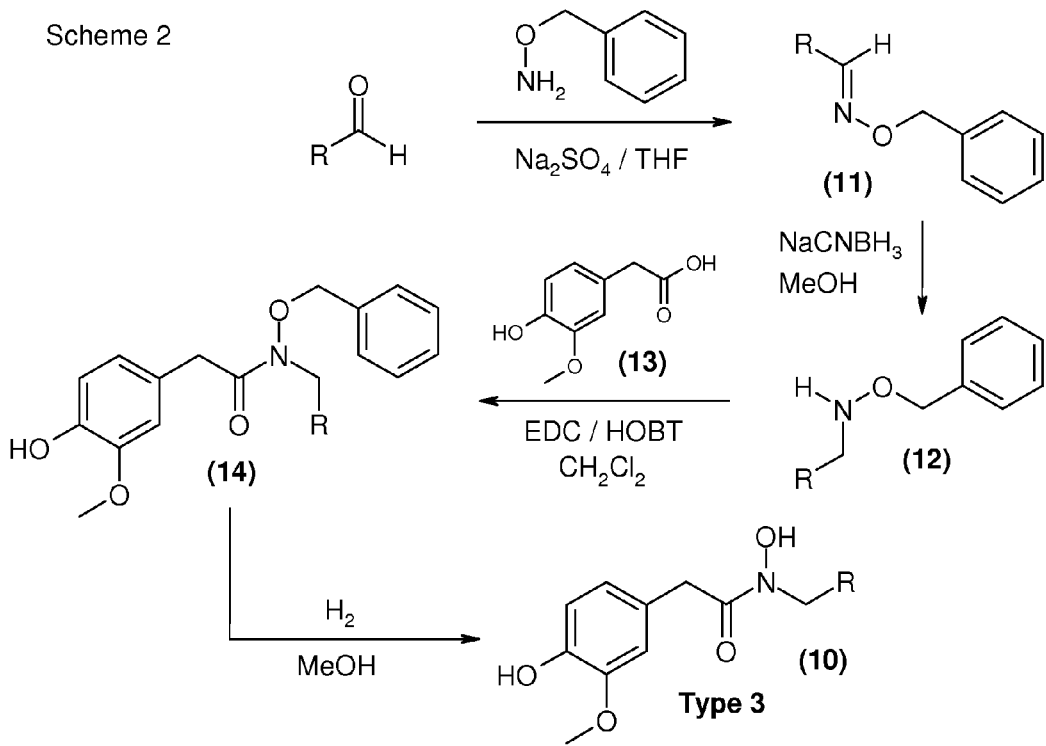
FIG. 3 shows in Scheme 2, an alternative synthetic route to compounds of Type 3.

The general scaffold for the compounds described in this invention, Formula (V) (also see FIG. 1), is highly flexible and embraces the N-hydroxybenzyl fatty carbamates of Type 1, the N-hydroxybenzyl fatty amides of Type 2, and the N-hydroxy aryl acetic acid amides with a pendant alkyl moiety (Type 3). All three of these classes contain the structural motifs often associated with potential MMP-9 inhibitors, including the hydroxamic acid construct, the electron-rich aryl group, and the lipophilic zone. The synthetic routes to these materials are outlined in FIGS. 2 and 3 (Schemes 1 and 2, respectively).

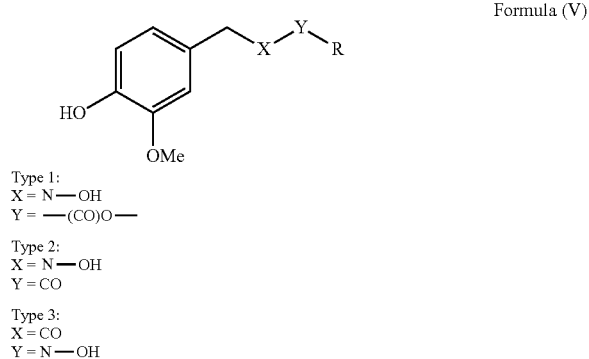

Formula (V)

Type 1:
X = N—OH
Y = —(CO)O—

Type 2:
X = N—OH
Y = CO

Type 3:
X = CO
Y = N—OH

One embodiment of the present invention is directed to a vanilloid fatty N-hydroxy amide or a vanilloid fatty N-hydroxy carbamate compound represented by Formula, where R is a lipophilic moiety selected from the group consisting of linear and branched alkyl, optionally branched cycloalkyl, linear and branched alkenyl, optionally branched cycloalkenyl, linear and branched alkynyl, optionally substituted aryl, optionally substituted heteroaryl, optionally substituted heteroarylalkyl, and optionally substituted arylalkyl and where either:
(1) X is NOH and Y is (C=O)O (Type 1), or
(2) X is NOH and Y is C=O (Type 2), or
(3) X is C=O and Y is NOH (Type 3). All of these compounds are hydroxamic acids, having the substructure —CO—N(OH)—.

The lipophilic R groups preferably contain 1 to 30 carbon atoms, preferably 2 to 24, more preferably 4 to 20, and most preferably 6 to 18 carbon atoms. Each aryl group independently comprises 6 to 19, preferably 6 to 10 carbon atoms, where the ring system is optionally partially saturated. Each heteroaryl group independently is a 5- to 18-membered, preferably a 5- to 10-membered aromatic ring system, which consists of carbon atoms and from one to five hetero-atoms selected from the group consisting of nitrogen, oxygen and sulfur. Each linking alkyl moiety in the arylalkyl and heteroarylalkyl groups is independently a straight or branched hydro-carbon chain consisting solely of carbon and hydrogen atoms, containing no unsaturation, having 1 to 12, preferably 1 to 6 carbon atoms. Optional substituents for the aryl, arylalkyl, heteroaryl and heteroarylalkyl groups include 1 to 5 substituents independently selected from the group consisting of halogen, hydroxy, C1-C6 alkyl, C1-C6 alkoxy, C1-C6 alkylthio, C1-C6 haloalkyl, C1-C6 haloalkoxy, and C1-C6 haloalkylthio. Further, the alkyl, cycloalkyl, alkenyl, cyclo-alkenyl, and alkynyl R-groups may optionally be independently substituted with 1 to 5 halogen, alkoxy and/or haloalkoxy groups.

Type 1 compounds are preferably selected from the group consisting of alkyl-N-hydroxy-N-4-hydroxy-3-methoxybenzylcarbamates. Type 2 compounds are preferably selected from the group consisting of N-hydroxy-N-4-hydroxy-3-methoxybenzylcarboxamides. Type 3 compounds are preferably selected from the group consisting of N-hydroxy-N-alkyl-(4-hydroxy-3-methoxy-phenyl)acetamides. A further embodiment of the invention includes prodrugs or pharmaceutically acceptable salts of the compounds of Formula (V). Pharmaceutically acceptable salts include, without limitation, acetate, benzoate, methanesulfonate, benzenesulfonate, and hydrochloride salts. Prodrugs are molecules which are capable of releasing in vivo an analog fitting the structural composition embodied in Formula (V). Examples of prodrugs include, without limitation, derivatives of the hydroxamic acid moiety —CO—N(OH)—, including O-acylated and O-carbamoylated analogs, formed, for example, by reaction of the N(OH) group with acylating agents (such as acyl halides, carboxylic acid anhydrides, or haloformate esters) or carbamoylating agents (e.g., carbamoyl halides or isocyanates).

Another aspect of the invention is directed to a method for preparing a compound of Type 1, comprising the step of reacting a benzylic hydroxylamine with a chloroformate or related acylating agent in the presence of magnesium oxide to direct acylation onto the nitrogen atom of the hydroxylamine and thereby yield an alkyl-N-hydroxy-N-benzylcarbamate of formula

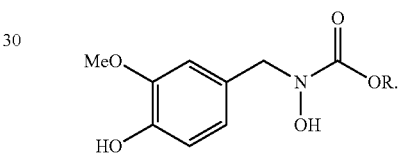

A further aspect of the invention is directed to a method for preparing a compound of Type 2, comprising the step of reacting a benzylic hydroxylamine with an acylated 2-mercapto-thiazoline or other activated acylating agent to direct acylation onto the nitrogen atom of the hydroxylamine and thereby yield an N-hydroxy-N-benzylcarboxamide of formula

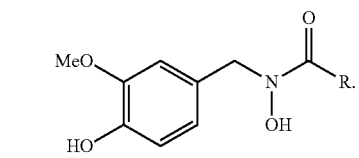

Another aspect of the invention is directed to a method for preparing a compound of Type 3, comprising the steps of:
(a) condensing an aliphatic aldehyde with an O-benzylhydroxylamine to form an oxime, where the O-benzyl group optionally can be substituted;
(b) reducing the oxime to the corresponding O-benzylhydroxylamine;
(c) condensing the O-benzylhydroxyamine with homovanillic acid (4-hydroxy-3-methoxyphenylacetic acid) in the presence of an appropriate condensing agent, to form an amide; and
(d) subjecting the amide to hydrogenolysis to cleave the O-benzyl group and thereby yield the N-hydroxy-N-alkyl (4-hydroxy-3-methoxyphenyl)acetamide of formula

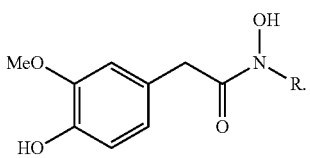

Hydrogenolysis may, for example, include hydrogenation over a suitable catalyst such as platinum oxide, palladium oxide, platinum on carbon or palladium on carbon.

Additional aspects of the invention are drawn to various methods of treatment, including:

A method for treatment of a disease state which is influenced by the regulation of FAAH, comprising administering to a patient in need thereof an amount of one or more of the above compounds effective to inhibit fatty acid amide hydrolase (FAAH);

A method for treatment of a disease state in which the regulation of MMP-9 is desired, comprising administering to a patient in need thereof an amount of one or more of the above compounds effective to inhibit matrix metalloproteinase-9 (MMP-9);

A method for treatment of a disease state in which the regulation of an inflammatory response is desired, comprising administering to a patient in need thereof an amount of one or more of the above compounds effective to suppress one or more inflammatory responses;

A method for treatment of a disease state in which inhibition of the separation of the ocular or cutaneous epithelium and stromal layers of the eye is desired, comprising administering to a patient in need thereof an amount of one or more of the above compounds effective to inhibit the separation of the ocular or cutaneous epithelium and stromal layers of the eye; wherein the compound can be formulated as an ophthalmic solution and can be applied topically via dropwise application to the eye;

A method for treatment of a topical or systemic disease state in which inhibition of an inflammatory dysfunction is desired, comprising administering to a patient in need thereof an amount of one or more of the above compounds effective to modulate an inflammatory dysfunction, wherein the compound can be formulated in a dosage form effective to deliver the compound to a desired site;

A method for treatment of injury to skin and/or eyes produced by vesicating agents, corrosive chemicals, or damage-producing substances, comprising administering to a patient in need thereof, an amount of one or more of the above compounds effective to function as an antagonist of the injury caused by vesicating agents, corrosive chemicals, or damage-producing substances, wherein the compound is optionally formulated for effective delivery to the injured site; and A method for treatment of ocular injury produced by vesicating agents, corrosive chemicals, or damage-producing substances, comprising administering to a patient in need thereof, an amount of one or more of the above compounds effective to relieve the ocular injury, wherein the compound can be formulated as an ophthalmic solution and can be applied topically via dropwise application to the eye.

EXAMPLES

General Procedure for the Preparation of N—OH Carbamates (Type 1). See Scheme 1

Preparation of Type 1 Carbamates

Step 1: Reduction of Vanillin Oxime to 4-((hydroxyamino)methyl)-2-methoxyphenol (Compound 1)

Sodium cyanoborohydride (1.88 g, 29.9 mmol) was added to a solution of 1.00 g, 6.0 mmol, of vanillin oxime (Sigma-Aldrich) in methanol (15 mL). Two drops of methyl orange indicator were added followed by dropwise addition of concentrated hydrochloric acid, until the solution remained pink and milky for at least 0.5 h. The reaction mixture was stirred at room temperature overnight and the solvent was removed under vacuum. The residue was taken up in dichloro-methane (100 mL) and washed until alkaline with 1 M potassium hydroxide solution and the aqueous portion extracted with dichloromethane (3×100 mL). The combined organic extracts were dried with $MgSO_4$, filtered and the solvent was evaporated to ca 10 mL and chilled to precipitate the product. Usually the reduced oxime is obtained in pure form (mp=144-146° C.). If additional purification is needed, chromatography on a silica gel column with dichloro-methane/methanol (95:5) as the mobile phase produced a highly purified product (1). Yields ranged from 58-70%. $^1$H NMR ($CDCl_3$) δ 6.88-6.82 (m, 3H), 3.98 (s, 2H) and 3.88 (s, 3H).

Step 2: Condensation of 4-((hydroxyamino)methyl)-2-methoxyphenol (1) with chloroformates (2), (Compounds 4)

Compound 1 (150 mg, 0.90 mmol) was added to a round bottom flask and 10 mL of 3:2 methanol:water mixture was added to it. The first charge of 1 mmol of magnesium oxide was added to that solution and stirred at room temperature for 5 minutes. Independently, a second solution was prepared from the requisite chloroformate (2) (1 mmol), 5 mL of THF and an additional 2 mmol of magnesium oxide (suspension). The chloroformate solution (with suspended MgO) was added to the reduced oxime (hydroxylamine) solution in the round bottom flask and stirred overnight. The solvent was removed under vacuum and the organic product taken up in ethyl acetate (3×50 mL washings of the MgO). The ethyl acetate phase was dried over anhydrous $MgSO_4$ and concentrated. The residue was purified using silica gel column chromatography with 1:1/hexane-ethyl acetate as the mobile phase to yield purified carbamates of Type 1 in isolated yields of 55-75%. $^1$H-NMR and exact parent ion mass spectrometry confirmed the structures. The reaction is successful for linear or branched, saturated or unsaturated alkyl chloroformates with R in 2 ranging from 1 to 18 carbons. As exemplars of this synthesis the following specific compounds are reported.

Synthesis of Hexadecyl-N-hydroxy(4-hydroxy-3-methoxybenzyl)carbamate, Compound 4a. (R=n-hexadecyl)

$^1$H NMR ($CDCl_3$) δ 6.87-6.80 (m, 3H), 5.63 (bs, 1H), 5.56 (s, 1H), 4.59 (s, 2H), 4.17 (t, 2H, $^3$J=6.75 Hz), 3.87 (s, 3H), 1.69-1.62 (m, 2H), 1.37-1.19 (m, 26H) and 0.86 (t,

Synthesis of Dodecyl-N-hydroxy(4-hydroxy-3-methoxybenzyl)carbamate, Compound 4b. (R=n-dodecyl)

$^1$H NMR (CDCl$_3$) δ 6.87-6.80 (m, 3H), 5.77 (bs, 1H), 5.57 (s, 1H), 4.59 (s, 2H), 4.16 (t, 2H, $^3$J=6.75 Hz), 3.87 (s, 3H), 1.68-1.63 (m, 2H), 1.37-1.19 (m, 18H) and 0.86 (t, 3H, $^3$J=6.9 Hz). Exact mass (ESI) calculated for C$_{21}$H$_{36}$NO$_5$ [M+H] 382.2588. Found 382.2582. Yield=72%.

Synthesis of Octyl-N-hydroxy(4-hydroxy-3-methoxybenzyl)carbamate, Compound 4c. (R=n-octyl)

$^1$H NMR (CDCl$_3$) δ 6.88-6.78 (m, 3H), 6.24 (bs, 1H), 5.60 (s, 1H), 4.58 (s, 2H), 4.15 (t, 2H, $^3$J=6.7 Hz), 3.86 (s, 3H), 1.69-1.60 (m, 2H), 1.33-1.16 (m, 10H) and 0.86 (t, 3H, $^3$J=7.1 Hz). Exact mass (ESI) calculated for C$_{17}$H$_{28}$NO$_5$ [M+H] 326.1962. Found 326.1960. Yield=68%.

Synthesis of Hexyl-N-hydroxy(4-hydroxy-3-methoxybenzyl)carbamate, Compound 4d. (R=n-hexyl)

$^1$H NMR (CDCl$_3$) δ 6.86-6.79 (m, 3H), 6.19 (bs, 1H), 5.59 (s, 1H), 4.58 (s, 2H), 4.15 (t, 2H, $^3$J=6.7 Hz), 3.86 (s, 3H), 1.67-1.62 (m, 2H), 1.37-1.19 (m, 6H) and 0.90-0.80 (m, 3H). Exact mass (ESI) calculated for C$_{15}$H$_{24}$NO$_5$ [M+H] 298.1649. Found 298.1653. Yield=65%.

Synthesis of 2-Ethylhexyl-N-hydroxy(4-hydroxy-3-methoxybenzyl)carbamate, Compound 4e. (R=2-ethylhexyl)

$^1$H NMR (CDCl$_3$) δ 6.89-6.77 (m, 3H), 6.16 (bs, 1H), 5.59 (s, 1H), 4.58 (s, 2H), 4.12-4.03 (m, 2H), 3.86 (s, 3H), 1.39-1.16 (m, 9H) and 0.90-0.82 (m, 6H). Exact mass (ESI) calculated for C$_{17}$H$_{28}$NO$_5$ [M+H] 326.1926. Found 326.1954. Yield=58%.

Synthesis of 2-Methoxyethyl-N-hydroxy(4-hydroxy-3-methoxybenzyl)carbamate, Compound 4f. (R=CH$_2$CH$_2$OCH$_3$)

$^1$H NMR (CDCl$_3$) δ 6.86-6.80 (m, 3H), 6.26 (bs, 1H), 5.62 (s, 1H), 4.59 (s, 2H), 4.30 (m, 2H), 3.86 (s, 3H), 3.61 (m, 2H), 3.34 (s, 3H). Exact mass (ESI) calculated for C$_{12}$H$_{18}$NO$_6$ [M+H] 272.1129. Found 272.1138. Yield=55%.

Synthesis of Phenyl-N-hydroxy(4-hydroxy-3-methoxybenzyl)carbamate, Compound 4g. (R=phenyl)

$^1$H NMR (CDCl$_3$) δ 7.38-7.34 (m, 2H), 7.24-7.21 (m, 1H), 7.12-7.10 (m, 2H), 6.89 (s, 3H), 6.07 (bs, 1H), 5.61 (s, 1H), 4.74 (s, 2H) and 3.87 (s, 3H). Exact mass (ESI) calculated for C$_{15}$H$_{16}$NO$_5$ [M+H] 290.1023. Found 290.1030. Yield=59%.

General Procedure for the Preparation of N—OH Vanilloid Amides (Type 2). See Scheme 1

Preparation of Type 2 Amides (Compounds 5)

In Step 1, the requisite acylated mercaptothiazolides (Compounds 3) were prepared from the reaction of equimolar quantities of the alkanoyl chloride and 2-mercaptothiazoline as bright yellow solids or oils as described by Nagao in 65-85% yields. In a second step, a condensation with an equimolar quantity of Compound 1 was brought about by stirring in dichloromethane with triethyl amine catalyst for 12-15 hours. Yields on the second step are 55-75%. Typical reactant mixtures in Step 1 consist of 5-7 mmol each of alkanoyl chloride, 2-mercaptothiazoline, and triethyl amine in 20-40 mL of dichloromethane. In Step 2, equimolar quantities of 1.2 to 2.0 mmol each of 1, 3, and triethyl amine were combined in 30-40 mL of dichloromethane. Linear and branched, saturated or unsaturated acid chlorides, ranging from acetyl to octadecanoyl are suitable to use in syntheses of the acylthiazolides 3 thereby providing diversity at R in the hydroxamates of Type 2 (Compounds 5) products. As exemplars of this synthesis the following specific compounds are reported.

Synthesis of (9Z)—N-Hydroxy-N-[(4-hydroxy-3-methoxyphenyl)methyl]-9-Octadecenamide, Compound 5a (R=8Z-heptyldecenyl)

To a 100 mL round bottom flask equipped with a stirring bar was added oleoyl chloride (2.00 g, 6.65 mmol). 2-Mercaptothiazoline (1.31 g, 6.33 mmol) was added followed by anhydrous dichloromethane (20 mL). Triethyl amine (0.88 mL, 6.33 mmol) was added in one shot. The reaction was stirred overnight. The next day, after TLC analysis, the reaction mixture was diluted with dichloromethane and washed with 1N HCl. The two layers were separated and the organic layer was washed with brine. The dichloromethane layer obtained was dried over anhydrous magnesium sulfate. Dichloromethane was evaporated to obtain the yellow oily crude product. The product was purified by silica gel column chromatography using 5% ethyl acetate-hexane mixture as eluent to render 87% yield of yellow oil: R$_f$=0.38, CH$_2$Cl$_2$/hexanes, 4:6, v/v.

Oleoyl thiazolide 3a (500 mg, 1.30 mmol) was added to a solution of reduced vanillin oxime (1) (232 mg, 1.37 mmol) in 35 mL dichloromethane. The resulting solution was stirred and (18 μL, 1.30 mmol) of triethyl amine was added. The reaction was stirred overnight. The reaction mixture was diluted with dichloromethane and extracted with 3×50 ml of 1N HCl and washed with saturated sodium chloride solution. The organic layer was dried using anhydrous magnesium sulfate, filtered, and concentrated. The oily residue was purified by silica gel column chromatography using EtOAc/hexanes, 3:7, v/v to give Compound 5a in 66% yield. $^1$H NMR (CDCl$_3$) δ 6.88-6.75 (m, 3H), 5.36-5.28 (m, 2H), 4.72 (s, 2H), 3.87 (s, 3H), 1.98 (d, J=6.15 Hz, 4H), 1.64 (s, 2H), 1.54 (s, 2H), 1.27-1.24 (m, 22H), 0.86 (t, J=6.55 Hz, 3H).

Synthesis of N-hydroxy-N-(4-hydroxy-3-methoxybenzyl)undec-10-enamide, Compound 5b (R=9-decenyl)

Compound 5b was prepared as described, mutatis mutandis, for 5a in 52% yield. $^1$H NMR (CDCl$_3$) δ 6.88-6.74 (m, 3H, Ar), 5.82-5.74 (m, 1H, C$\underline{H}$=CH$_2$), 4.98-4.89 (m, 2H, CH=C$\underline{H}_2$), 3.78 (s, 3H, ArOC$\underline{H}_3$), 2.29-2.26 (m, 2H, COC$\underline{H}_2$), 2.03-1.99 (m, 2H, $\underline{H}$H$_2$CH=CH$_2$), 1.64-1.53 (m, 2H, COCH$_2$C$\underline{H}_2$) and 1.39-1.20 (m, 10H, aliphatic).

Synthesis of 2-hexyl-N-hydroxy-N-(4-hydroxy-3-methoxybenzyl)decanamide, Compound 5c (R=nonyl)

Compound 5c was prepared as described, mutatis mutandis, for 5a in 54% yield. $^1$H NMR (CDCl$_3$) δ 7.72 (bs, 1H), 6.90-6.75 (m, 3H, Ar), 4.04 (s, 2H, Ar—C$\underline{H}_2$), 3.88 (s, 3H, ArOC$\underline{H}_3$), 2.32-2.28 (m, 1H, COC$\underline{H}$), 1.60-1.48 (m, 2H, CH—C$\underline{H}_2$), 1.43-1.32 (m, 2H, CH—C$\underline{H}_2$), 1.32-1.08 (m, 20H, aliphatic) and 0.88-0.79 (m, 6H, 2 C$\underline{H}_3$).

General Procedure for the Preparation of N—OH Vanilloid Amides (Type 3). See Schemes 1 and 2

Pathways to Type 3: Option 1 (see Scheme 1)

Shown in Scheme 1 is a thiazolide route for Type 3 products. While the syntheses of the requisite hydroxyamines 8 from the aldehydes 6 via the oximes 7 proceeded in excellent yield, the condensation step proved problematic because of instability in the starting material 9. This route is the parallel to the highly successful one shown above in Scheme 1 and used by us for Type 2 products. This amide-forming reaction has strong precedent in the literature wherein a thiazoline is used as an activating group of a carboxylic acid for aminolysis. In our hands, however, the particular thiazolide of homovanillic acid 9 (wherein Ar=4-hydroxy-3-methoxy-phenyl) proved unstable, possibly as a consequence of the presence of the phenolic hydroxyl. Preparation of 9 following the known method proceeded in good yield and initially TLC showed one major spot, apparently >80%. However, the column chromatography necessary to obtain pure material resulted in extensive decomposition. If this pathway had succeeded it would have constituted an advantage in that we would have been to be able to prepare the activated amide 9 and then use the disappearance of its yellow color as an indicator of completion of reaction with a hydroxylamine. This technique did work well for the synthesis of the Type 2 N-hydroxyamide. Furthermore, acylthiazolides are known to react specifically at the nitrogen of hydroxylamines (as demonstrated by us, see Scheme 1, for the synthesis of Type 2 compounds). Because of the instability of 9 we adopted an alternative synthesis, see Scheme 2 and Option 2 (below).

Pathways to Type 3: Option 2 (see Scheme 2)

General description of Syntheses of N-alkyl-N-hydroxy-2-(4-hydroxy-3-methoxyphenyl)acetamides (Type 3) (Compounds 10)

Since homovanillic acid thiazolide 9 could not be prepared in isolable quantity, the synthesis of the retrohydroxamates, viz. compounds Type 3, structure 10 was carried out from O-benzylhydroxyamine in four steps. In Step 1, the appropriate oxime 11 was first synthesized by neat reaction of the aldehyde of choice with O-benzylhydroxyamine at room temperature. In Step 2, reduction of this oxime 11 with sodium cyanoborohydride yielded the alkylated O-benzylhydroxylamine 12. In Step 3, coupling of the alkylated O-benzylhydroxylamine 12 to homovanillic acid 13 was carried out using EDC,HCl (also known as N-3-dimethylaminopropyl-N'-ethylcarbodiimide hydrochloride) and HOBt (also known as hydroxybenzotriazole) to yield 14. In Step 4 the final product was then obtained by hydrogenolysis of 14 to yield free hydroxyamate 10. The final step was achieved in yields of 75-85% and the materials were characterized by $^1$H NMR and exact mass spectrometry. It should be noted each of the above steps included chromatographic purification. This reaction is versatile and can be commenced with linear or branched, saturated or unsaturated aldehydes ranging from acetaldehyde to hexadecanal.

Synthesis of N-(benzyloxy)heptan-1-imine, Compound 11a (R=n-hexyl)

To a 10 mL round bottom flask equipped with a stifling bar and purged with $N_2$ was added heptanal (343 mg, 420 μL, 3.0 mmol) followed by O-benzylhydroxylamine (369 mg, 349 μL, 3.0 mmol). An immediate evolution of heat occurred with formation of a cloudy solution. The solution was stirred at room temperature during four minutes before 3 mL of dry THF was added. Stirring continued for 20 min, at which time the TLC (hexanes/ethyl acetate, 85:15) indicated completion of reaction. The volatiles were removed under reduced pressure, and the crude material was purified by column chromatography on silica gel using hexanes/ethyl acetate (95:5) as eluent to give 599 mg (91%) of clear oil: $R_f$=0.48 and 0.51 (two isomers) (hexanes/ethyl acetate, 95:5, v/v); $^1$H NMR (CDCl$_3$) δ 7.43 (t, $^3$J=6.3 Hz, 0.6H), 7.36-7.31 (m, 4H), 7.30-7.26 (m, 1H), 6.66 (t, $^3$J=5.3 Hz, 0.4H), 5.09 (s, 0.8H), 5.04 (s, 1.2H), 2.37-2.33 (m, 0.8H), 2.19-2.15 (m, 1.2H), 1.48-1.42 (m, 2H), 1.34-1.23 (m, 6H), and 0.86 (t, $^3$J=7.0 Hz, 3H).

Synthesis of N-(benzyloxy)heptan-1-amine, Compound 12a (R=n-hexyl)

Oxime 11a (570 mg, 2.60 mmol) was dissolved in 15 mL of HPLC grade methanol. To the stirred solution was added a tiny portion of methyl orange indicator and then NaCNBH$_3$ (817 mg, 5×2.60 mmol). Dropwise addition of concentrated HCl, at intervals, was carried out until the pink color persisted for 0.5 h. [Note: The addition of acid required approximately 2 h] The mixture was stirred overnight at room temp. The methanol was removed under reduced pressure in a fume hood. The dry residue was taken up in 100 mL of CH$_2$Cl$_2$ and the resulting solution extracted with 75 mL of 1N KOH. The aqueous layer was extracted with 2×40 mL of CH$_2$Cl$_2$. The organic extracts were combined and dried over MgSO$_4$, filtered and concentrated. Purification by column chromatography on silica gel eluting with CH$_2$Cl$_2$/hexanes (9:1) gave 475 mg (83%) of a clear oil: $R_f$=0.36 (dichloromethane/hexanes, 95:5, v/v); $^1$H NMR (CDCl$_3$) δ 7.36-7.28 (m, 5H), 4.77 (s, 2H), 2.96-2.93 (m, 2H), 1.57-1.51 (m, 2H), 1.33-1.22 (m, 8H) and 0.86 t, $^3$J=7.0 Hz, 3H). Exact mass (FAB$^+$) calculated for C$_{14}$H$_{24}$NO [M+H] 222.1852. Found 222.1861.

Synthesis of N-benzyloxy-N-heptyl-2-(4-hydroxy-3-methoxyphenyl)acetamide, Compound 14a (R=n-hexyl)

A flask was charged with a solution of homovanillic acid (13) (182 mg, 1.0 mmol), HOBt (142 mg, 1.05 mmol), N-benzyloxyheptylamine 12a (232 mg, 1.05 mmol) and 10 mL of dry CH$_2$Cl$_2$. To the stirred solution was added EDC, HCl (211 mg, 1.1 mmol), and stifling continued overnight. The reaction solution was diluted with CH$_2$Cl$_2$ and extracted with 1N HCl, saturated NaHCO$_3$ and saturated NaCl, and the resulting organic layer was dried over MgSO$_4$, filtered and concentrated. The residue was purified by column chromatography on silica gel eluting first with CH$_2$Cl$_2$, then CH$_2$Cl$_2$/EtOH (98:2) and finally CH$_2$Cl$_2$/MeOH (98:2) to give 358 mg (93%) of a clear oil: $R_f$=0.33 (dichloromethane/methanol, 98:2, v/v); $^1$H NMR (CDCl$_3$) δ 7.38-7.33 (m, 5H) 6.80 (d, $^3$J=8.0 Hz, 1H), 6.74 (bs, 1H), 6.68 (dd, $^3$J=8.0 Hz, $^4$J=1.5 Hz), 5.48 (bs, 1H, —OH), 4.74 (s, 2H), 3.78 (s, 3H), 3.62 (bs, 4H), 1.60-1.58 (m, 2H), 1.26-1.17 (m, 8H)

and 0.84 (t, $^3J$=7.0 Hz, 3H). Exact mass (FAB$^+$) calculated for $C_{23}H_{32}NO_4$ [M+H] 386.2356. Found 386.2309.

Synthesis of N-heptyl-N-hydroxy-2-(4-hydroxy-3-methoxyphenyl)acetamide, 10a (R=hexyl)

To a 3-neck round bottom flask containing a stirring bar and palladium on carbon (5%) was added a solution of 14a (358 mg, 0.93 mmol) in 9.3 mL of dry MeOH. The suspension was stirred at room temperature and hydrogenolyzed at atmospheric pressure until uptake of $H_2$ was observed to have ceased (7 h). The suspension was filtered and the filtrate was concentrated. The crude product was purified by column chromatography on silica gel eluting with $CH_2Cl_2$/MeOH (98:2) to yield 216 mg (79%) of a brown solid (indicating complexation of iron): $R_f$=0.13 (dichloromethane/methanol, 98:2, v/v); $^1H$ NMR (CDCl$_3$) δ 6.93-6.69 (m, 3H), 3.88 (bs, 3H), 3.80-3.40 (bs, 4H), 1.75-1.50 (bs, 2H), 1.243 (bs, 8H) and 0.86 bs, 3H). Exact mass (FAB$^+$) calculated for $C_{16}H_{26}NO_4$ [M+H] 296.1856. Found 296.1860.

Synthesis of N-(benzyloxy)octan-1-imine, 11b (R=n-heptyl)

Octanal (385 mg, 469 µL, 3.0 mmol) was weighed into a 10 mL round bottom flask previously flushed with $N_2$ and containing a stifling bar. To the flask was anhydrous $Na_2SO_4$ (4.26 g, 30 mmol), 6 mL of dry dichloromethane and finally, O-benzylhydroxylamine (369 mg, 349 µL, 3 mmol) over 2 min while maintaining positive $N_2$ pressure. The reaction mixture was stirred overnight. The salt was filtered off and rinsed with dichloromethane. The combined filtrates and rinsings were concentrated. The crude material was purified by column chromatography on silica gel eluting with hexanes/ethyl acetate (95:5) to give 328 mg (47%) of a clear oil: $R_f$=0.45 and 0.51 (two isomers) (hexanes/ethyl acetate, 95:5, v/v); $^1H$ NMR (CDCl$_3$) δ 7.43 (t, $^3J$=6.3 Hz, 0.5H), 7.36-7.25 (m, 5H), 6.66 (t, $^3J$=5.5 Hz, 0.5H), 5.08 (s, 1H), 5.03 (s, 1H), 2.37-2.32 (m, 1H), 2.18-2.14 (m, 1H), 1.49-1.41 (m, 2H), 1.33-1.18 (m, 8H), and 0.86 (t, $^3J$=7 Hz, 3H). Exact mass (FAB$^+$) calculated for $C_{15}H_{24}NO$ [M+H] 234.1852. Found 234.1856.

Synthesis of N-(benzyloxy)octan-1-amine, 12b (R=n-heptyl)

The title compound was prepared exactly as described for the preparation of 12a. Oxime 11b (626 mg, 2.683 mmol), NaCNBH$_3$ (843 mg, 13.4 mmol), anhydrous methanol (15.5 mL), concentrated HCl and methyl orange indicator were reacted to give, after extractive workup (vide supra) and column chromatography (silica gel with dichloromethane as eluent) 465 mg (74%) of clear oil: $R_f$=0.54 (dichloromethane); $^1H$ NMR (CDCl$_3$) δ 7.36-7.25 (m, 5H), 5.52 (s, 1H, —NH), 4.69 (s, 2H), 2.91 (t, $^3J$=7.2 Hz, 2H), 1.51-1.44 (m, 2H), 1.33-1.16 (m, 10H) and 0.86 (t, $^3J$=6.9 Hz, 3H). Exact mass (FAB$^+$) calculated for $C_{15}H_{26}NO$ [M+H] 236.2009. Found 236.2016.

Synthesis of N-benzyloxy-N-octyl-2-(4-hydroxy-3-methoxyphenyl)acetamide, 14b (R=n-heptyl)

Amine 12b (247 mg, 1.05 mmol) was weighed into a round bottom flask containing a stirring bar and previously purged with $N_2$. To the flask were added homovanillic acid (13) (182 mg, 1.0 mmol) and HOBt (142 mg, 1.05 mmol). The system was placed under a positive $N_2$ pressure, and dry dichloromethane (10 mL) was added via a rubber septum. Stirring at room temperature continued until most of the material had dissolved, except for the HOBt. Once the EDC, HCl (211 mg, 1.1 mmol) was added, a clear solution obtained quickly, and the reaction solution was stirred for 4.5 hours, after which time TLC indicated completion of reaction. The reaction solution was diluted with $CH_2Cl_2$ and extracted with water, 1N HCl, saturated NaHCO$_3$ and saturated NaCl. The organic layer was dried over MgSO$_4$, filtered and concentrated. The residue was purified by column chromatography on silica gel eluting with $CH_2Cl_2$, $CH_2Cl_2$/EtOH (98:2) and finally $CH_2Cl_2$/MeOH (98:2) to give 375 mg (94%) of a clear oil: $R_f$=0.36 (dichloromethane/methanol, 98:2, v/v); $^1H$ NMR (CDCl$_3$) δ 7.4-7.31 (m, 5H), 6.80 (d, $^3J$=8.0 Hz, 1H), 6.74 (bs, 1H), 6.68 (dd, $^3J$=8.0 Hz, $^4J$=1.9 Hz, 1H), 5.49 (bs, 1H, —OH), 4.69 (s, 2H), 3.78 (s, 3H), 3.67-3.58 (m, 4H), 1.63-1.55 (m, 2H), 1.30-1.15 (m, 10H) and 0.85 (t, $^3J$=7.0 Hz, 3H). Exact mass (FAB$^+$) calculated for $C_{24}H_{34}NO_4$ [M+H] 400.2482. Found 400.2501.

Synthesis of N-octyl-N-hydroxy-2-(4-hydroxy-3-methoxyphenyl)acetamide, 10b (R=n-heptyl)

Compound 14b (370 mg, 0.926 mmol) was hydrogenolyzed as described for compound 14a (vide supra) during 8 hours, after which time no more hydrogen uptake was observed. Filtration, evaporation and drying, without the need for further purification, gave 224 mg (78%) of a lightly pink solid: $R_f$=0.14 (dichloromethane/methanol, 98:2, v/v); $^1H$ NMR (CDCl$_3$) δ 6.83 (d, $^3J$=8.0 Hz, 1H), 6.79 (bs, 1H), 6.68 (bd, $^3J$=7.9 Hz, 1H), 3.86 (s, 3H), 3.62-3.55 (m, 3H), 3.46 (s, 1H), 1.63-1.53 (bm, 2H), 1.31-1.16 (m, 10H) and 0.86 (t, $^3J$=6.9 Hz, 3H). Exact mass (FAB$^+$) calculated for $C_{17}H_{28}NO_4$ [M+H] 310.2013. Found 310.2025.

PHARMACEUTICAL UTILITY

Several in vitro and in vivo methods demonstrated the utility of the compounds described herein.

Inhibition of Matrix Metalloproteinase 9 (MMP-9)

The AnaSpec Colorimetric SensoLyte MMP Assay Systems #72095 for quantitative measurement of MMP-9 was employed in these studies. The assay was performed under instructions provided in the kit and results are reported as IC$_{50}$'s. All of the hydroxamates showed some inhibition of MMP-9 with the greatest responses being IC$_{50}$ of 68 µM for 10b, 99 µM for 5c, and 120 µM for 4a. Corresponding carbamates and amides lacking the N—OH displayed no activity up to the highest concentrations tested (700 µM). The hydroxamic acid 10b with the lowest IC$_{50}$ for inhibition of MMP-9 was also the most potent hydroxamate tested in the rabbit cornea assay.

Inhibition of Fatty Acid Amide Hydrolase (FAAH)

It is well recognized that the endocannabinoid system is a key lipid signaling pathway that has been implicated in many physiological processes including pain control, fat metabolism, neurological diseases and especially inflammation. Key endocannabinoids released from lipid precursors in this pathway include 2-arachidonoylglycerol and arachidonoylethanolamide. These signaling molecules are known to mediate their action in peripheral tissues, at least in part, by binding to the cannabinoid receptors CB1 and CB2. An enzyme known to be important in degrading endocannabinoid mediators including arachidonoylethanolamide and related fatty acid amides is the serine protease FAAH.

Inhibitors of this enzyme prevent degradation of endocannabinoids and of other fatty acid amides, thereby increasing the levels of these endogenous mediators or of therapeutic fatty amide-like pharmaceuticals and thus providing a clinical benefit.

We assayed our hydrorxamic acid amide as inhibitors of FAAH using an FAAH Inhibitor Screening Assay Kit from Cayman Chemical (Ann Arbor, Mich.). This kit provides a fluorescence-based method for screening FAAH inhibitors. In this assay, human recombinant FAAH hydrolyzes 7-amino-4-methylcoumarin (AMC)-arachidonoyl amide resulting in the release of the fluorescent product AMC. In our studies, AMC was quantified on a Molecular Devices M5 microplate reader using an excitation wavelength of 340 nm and an emission wavelength of 450 nm. Reactions in 0.2 ml were run as directed by the manufacturer for 30 min at 37° C. using 96 well plates with each well containing FAAH in 125 mM Tris-HCl buffer, pH 9.0 containing 1 mM EDTA and 20 micromolar (final concentration) of the substrate 7-amino-4-methylcoumarin (AMC)-arachidonoyl amide in the absence and presence of increasing concentrations of our candidate therapeutics. Data are presented as the concentration of candidate therapeutic inhibiting FAAH activity by 50% ($IC_{50}$). Significant FAAH inhibition was observed in many of the hydroxamates, viz. 4g 10 µM, 4b 67 µM, 4c 73 µM, 5a 71 µM, and 10a 192 µM.

In Vivo Inflammatory Suppression Assay in Rodents

The mouse ear vesicant model (MEVM) was employed to assess the anti-inflammatory activity of the N-hydroxycarbamates or N-hydroxyamides of Types 1, 2, and 3. This edema-based assay has been historically used to screen for inhibitors of inflammation and is well-described in the literature. In this assay, a sulfur mustard analog (CEES or 2-chloroethyl ethyl sulfide), or phorbol ester (TPA or 12-O-tetradecanoylphorbol-13-acetate) was applied topically to the ears of female CD-1 mice (24-25 days old) in 20 µL of dichloromethane or acetone to generate an inflammatory response. This is evident by the appearance of edema in the mouse ears. Edema is quantified by increases in the wet weight of ear punch biopsies. Anti-inflammatory agents can effectively suppress irritant-induced increases in ear weight. Mice were treated on the inner surface of the right ear with 20 µL of dichloromethane (control) or TPA (1.5 micromoles dissolved in 20 µL of dichloromethane) or CEES (65 micromoles dissolved in 20 µL of dichloromethane) and the test compounds (1 to 2 micromoles) per application. The test compounds were applied in a light, readily evaporated organic solvent such as acetone, dichloromethane, or methanol.

Then, six hours after exposure, all mice were sacrificed and the ear punches (6 mm in diameter) were taken and weighed. Data were analyzed as percent inhibition of the vesicant-induced edema. All of the N-hydroxy vanilloidcarbamates and N-hydroxyvanilloid amides suppressed the vesicant-induced inflammatory and edema injury. Typical results for percent suppression of inflammatory edema weight gain in punches from treated mice ears for cases in which TPA is the initiator are: 10a, 50% suppression; 10b, 49% suppression; and 5a, 64% suppression. Typical results for suppressions when CEES is the inflammatory inducer are: 4f, 80% suppression; 4c, 69% suppression, and 4g, 43% suppression.

Rabbit Cornea Organ Culture Assay

Figure 4:
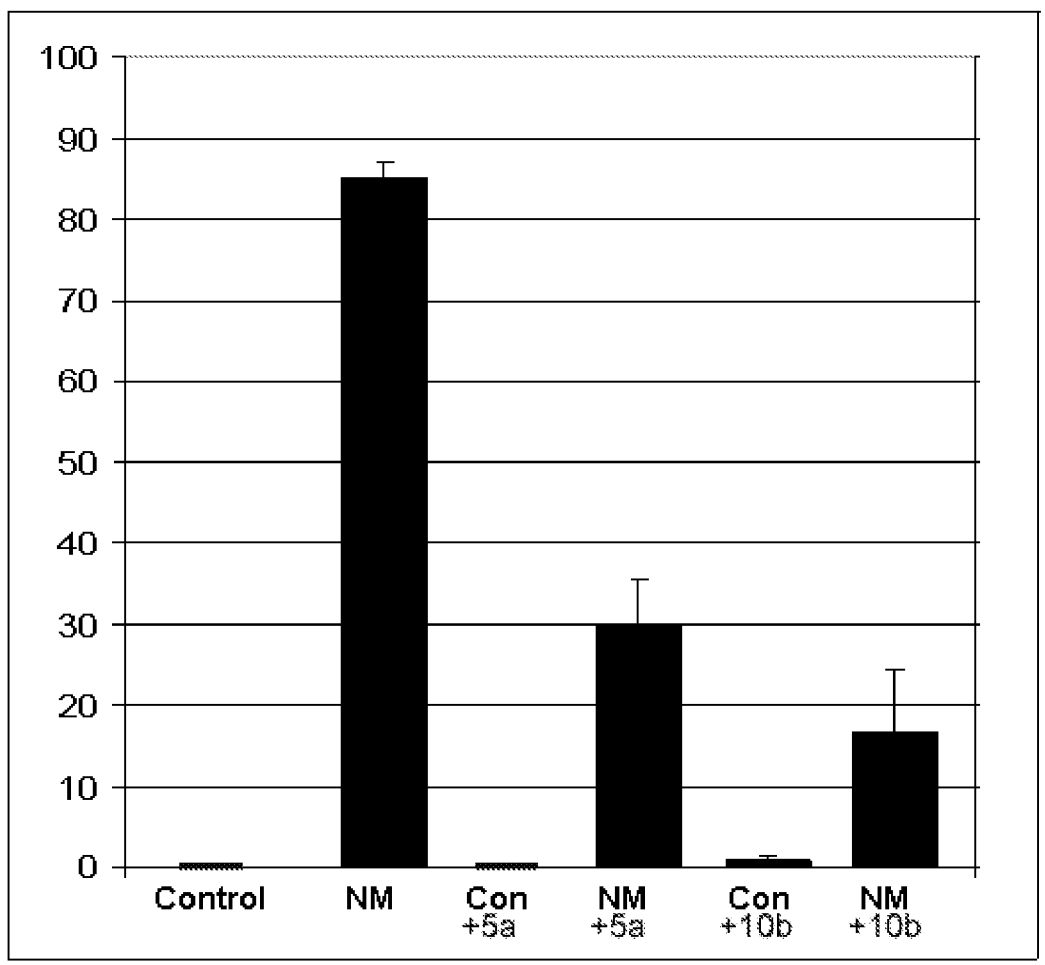
FIG. 4 shows a graph of the percentage of epithelial-stromal detachment vs. test specimen. NM=nitrogen mustard, Control (or Con)=an isotonic sterile eye drop medium containing buffer and PEG 400.

The known method in which freshly excised rabbit corneas containing a band of attached scleral tissue are filled with Agarose and submerged in a culture medium in a Petri dish up to the scleral rim was employed in these studies. A chemical irritant (200 nanomoles of CEES or 100 nanomoles of nitrogen mustard) was applied to the test corneas which were then incubated at 37° C. for 2 hours and then treated four times in the next 22 hours with a candidate pharmaceutical (in this case the vanilloid hydroxamic acid). The dose employed per treatment is 20 µL of a 20 micromolar solution of the hydroxamate in standard isotonic ocular media containing PEG 400 and buffer. The control cornea received only media. FIG. 4 shows the percentage of epithelial-stromal detachment on Y axis vs. test specimen on X axis where NM=nitrogen mustard, Control (or Con)=an isotonic sterile eye drop medium containing buffer and PEG 400.

Inspection of cornea cross sections with and without staining using Collagen XVII anti-bodies showed that members of hydroxamate Types 2 and 3 (especially 10b and 5a) displayed considerable protection against chemically-induced injury. When the basement membrane was subjected to microscopic inspection, the percentage of epithelial-stromal detachment (following a nitrogen mustard insult) was substantially less in eyes treated with the hydroxamates (see FIG. 4). These compounds are predicted to be beneficial in the treatment of recurrent corneal erosion, which is a painful ocular disorder characterized by the failure of the cornea's epithelial layer to remain attached to the underlying stromal layer.

Using nitrogen mustard alone to induce such an ocular affect demonstrated that only 15% of the basement membrane (i.e., 85% separation) was still attached after application. As shown in FIG. 4, with nitrogen mustard followed by treatment with the hydroxamates, substantially less epithelial-stromal detachment had occurred. The membrane was 70% attached post-treatment with 5a (i.e., 30% separation), and 85% attached post-treatment with 10b (i.e., 15% separation). Thus nitrogen mustard causes separation of the epithelial layer from the stromal layer. Compounds 5a and 10b preserve the attachment of the 2 cell layers.

Figure 5:
FIG. 5 displays electron micrographs of rabbit cornea damaged by nitrogen mustard and treated with compound 10b.
Figure 5:
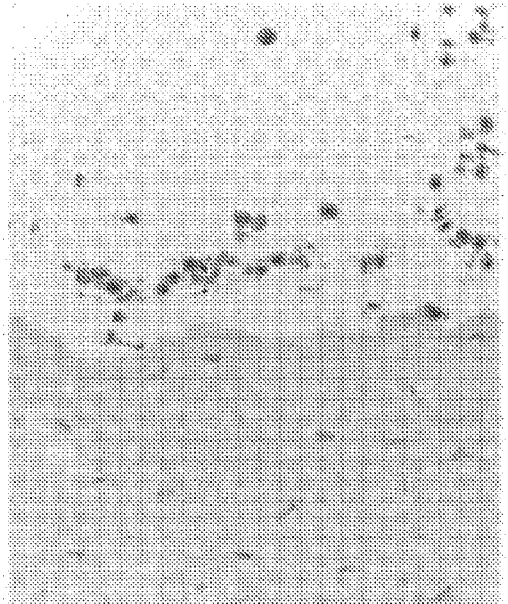
Figure 5:
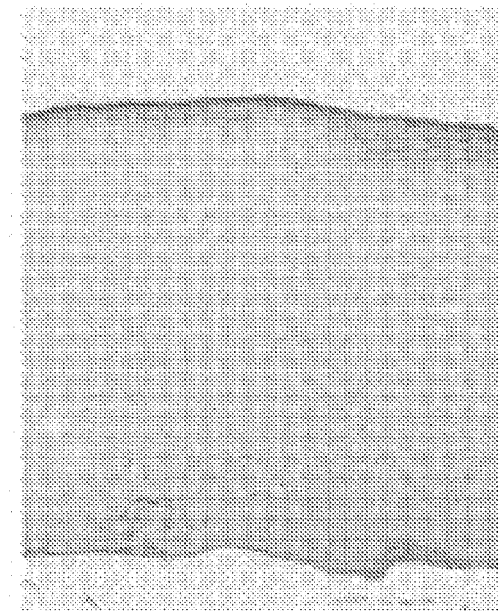
Figure 5:

FIG. 5 displays the electron micrographs of rabbit cornea damaged by nitrogen mustard and treated, as described above, with 10b. Similar results are observed with 5a.

DOSAGE FORMULATION

The drugs reported herein can be administered in effective amounts for the clinical conditions for which the substance is indicated by either oral, ophthalmic, or topical formulation. The concentration of the pharmaceutical in its formulated form can be established by one skilled in the art and will vary with the nature and severity of the dysfunction as well as the pharmacokinetics/pharmacodynamics and in vivo release of the substance.

The oral solid dosage—troches, capsules, or pills—normally contains excipients which provide dilution, extended release, and processing facility. Starch, alkylated celluloses, talc, lactose, silicon dioxide, and magnesium stearate are but a few of the performance enhancing additives. The principles for selection of the best excipient(s) for a given API are well documented and easily applied by one skilled in the arts.

Liquid oral dosage forms may also prove utilitarian. The active ingredient dissolved in a fatty oil in sealed capsules can provide a suitable gastric or enteric release. A syrup, elixir, or a suspension can also provide oral bioavailability.

Topical or ophthalmic formulations can include sterile water or saline, biocompatible polymers and oils, glycerine, or other suitable solvents with or without emulsifiers. Typical formulations include the drug substance dissolved in sterile water containing one or more of these additives carboxymethylcellulose, dextran, glycerin, hypromellose, polyethylene glycol 400 (PEG 400), polysorbate, polyvinyl alcohol, povidone, or propylene glycol, among others. Preservatives such as antioxidants, antibacterials, buffers, chelating agents, and tonicity modifiers (low molecular weight saccharides and sodium chloride) can also be included. While concentrations vary widely, the typical concentration of the active ingredient in the lipid, oil, cream, or lotion topical formulations is 1-4%.

Transdermal dosage forms are a special variant of topicals which contain penetration enhancers, skin softeners, and viscosity modulators blended with the pharmaceutically active substance on an impermeable backing with an edge-coated adhesive.

A word of caution regarding the manipulation or formulation of these N-hydroxycarbamates and amides. All of these substances are strong metal ion chelators. They bind zinc and iron (both ferrous and ferric) and most of the chelates display color. Deep red/purple complexes result from the combination of ferric iron and the lower molecular weight ligands reported herein, viz. 4f, 4g, 5c, and 10b. If distilled, deionized water is not used or highest purity solvents are not used, traces of the chelate are formed in the otherwise colorless white solids causing a pink-to-red hue.

The invention has been described in the various embodiments provided in the above Examples and the following claims, which are in no way intended to limit the scope of the present invention.

What is claimed is:

1. A vanilloid fatty N-hydroxy amide or vanilloid fatty N-hydroxy carbamate compound represented by Formula (V):

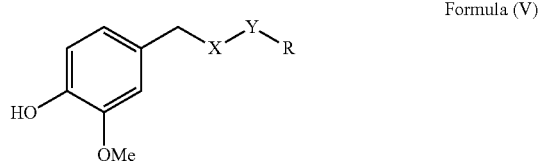

Formula (V)

wherein when (1) X is N(OH) and Y is C(=O)O, or (2) X is N(OH) and Y is C(=O), R is a lipophilic moiety selected from the group consisting of unsubstituted linear alkyl, branched alkyl, optionally branched cycloalkyl, linear alkenyl, branched alkenyl, optionally branched cycloalkenyl, linear alkynyl, branched alkynyl, optionally substituted aryl, optionally substituted heteroaryl, optionally substituted heteroarylalkyl, and optionally substituted arylalkyl; and when (3) X is C(=O) and Y is N(OH), R is a lipophilic moiety selected from the group consisting of unsubstituted linear alkyl, branched alkyl, optionally branched cycloalkyl, linear alkenyl, branched alkenyl, and optionally branched cycloalkenyl;

or the compounds of Formula (V) are prodrugs or pharmaceutically acceptable salts thereof.

2. The compound of claim 1, selected from the group consisting of alkyl-N-hydroxy-N-4-hydroxy-3-methoxybenzylcarbamates.

3. The compound of claim 1, selected from the group consisting of N-hydroxy-N-4-hydroxy-3-methoxybenzyl-carboxamides.

4. The compound of claim 1, selected from the group consisting of N-hydroxy-N-alkyl-(4-hydroxy-3-methoxyphenyl)acetamides.

5. The compound of claim 4 which is a prodrug or a pharmaceutically acceptable salt.

6. A method for preparing a compound according to claim 2, comprising the step of reacting a benzylic hydroxylamine with a chloroformate in the presence of magnesium oxide to direct acylation onto the nitrogen atom of the hydroxylamine and thereby yield an alkyl-N-hydroxy-N-benzylcarbamate of formula

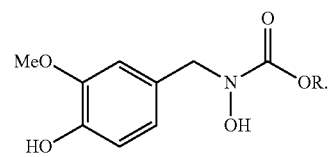

7. A method for preparing a compound according to claim 3, comprising the step of reacting a benzylic hydroxylamine with an acylated 2-mercaptothiazoline to direct acylation onto the nitrogen atom of the hydroxylamine and thereby yield an N-hydroxy-N-benzyl-carboxamide of formula

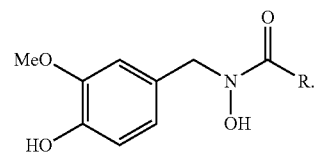

8. A method for preparing a compound according to claim 4, comprising the steps of:
(a) condensing an aliphatic aldehyde with O-benzylhydroxylamine to form an oxime,
(b) reducing the oxime to an O-benzylhydroxylamine,
(c) condensing the O-benzylhydroxyamine with homovanillic acid (4-hydroxy-3-methoxyphenylacetic acid) to form an amide, and
(d) subjecting the amide to hydrogenolysis to cleave the O-benzyl group and thereby yield the N-hydroxy-N-alkyl(4-hydroxy-3-methoxyphenyl)acetamide of formula

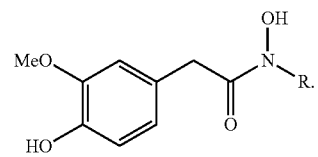

9. The compound of claim 1, wherein said pharmaceutically acceptable salt is selected from the group consisting of acetate, benzoate, methanesulfonate, benzenesulfonate, and hydrochloride salts.

10. The compound of claim 1, wherein said prodrug is selected from the group consisting of O-acylated and O-carbamoylated derivatives of the hydroxamic acid moiety.

11. The compound of claim 5, wherein said pharmaceutically acceptable salt is selected from the group consisting of acetate, benzoate, methanesulfonate, benzenesulfonate, and hydrochloride salts.

12. The compound of claim 5, wherein said prodrug is selected from the group consisting of O-acylated and O-carbamoylated derivatives of the hydroxamic acid moiety.

* * * * *